United States Patent [19]

Hattori et al.

[11] Patent Number: 4,918,248

[45] Date of Patent: Apr. 17, 1990

[54] PROCESS FOR PREPARATION OF ALCOHOLS

[75] Inventors: Yasuyuki Hattori; Noriaki Fukuoka; Shigeru Tamura; Kunizo Hashiba; Kiyoshi Tsukada, all of Wakayama; Makoto Misono, Tokyo, all of Japan

[73] Assignee: Kao Corporation, Tokyo, Japan

[21] Appl. No.: 355,292

[22] Filed: May 22, 1989

[30] Foreign Application Priority Data

Jun. 2, 1988 [JP] Japan ................................. 63-136563

[51] Int. Cl.⁴ .................... C07C 29/136; C07C 31/125
[52] U.S. Cl. .................................... 568/885; 502/345; 568/811; 568/814; 568/831; 568/864
[58] Field of Search ............... 568/885, 864, 831, 514, 568/811

[56] References Cited

U.S. PATENT DOCUMENTS

| | | | |
|---|---|---|---|
| 2,093,159 | 9/1937 | Schmidt | 568/885 |
| 3,197,418 | 7/1965 | Maebashi et al. | 568/885 |
| 3,370,067 | 2/1968 | Johnson | 568/885 |
| 4,398,039 | 8/1983 | Pesa et al. | 568/885 |
| 4,524,225 | 6/1985 | Qualeatti et al. | 568/885 |
| 4,628,128 | 12/1986 | Bartley | 568/885 |
| 4,628,129 | 12/1986 | Bartley | 568/885 |

Primary Examiner—J. E. Evans

[57] ABSTRACT

An alcohol is effective produced by catalytically reducing an organic carboxylic acid ester with hydrogen in the presence of a catalyst obtained by reducing a catalyst precursor comprising (A) copper oxide and (B) titanium oxide and/or titanium hydroxide at a weight ratio of (A) to (B) in the range between 15/85 and 65/35. The component (A) may be alternatively a composite metal oxide comprises copper oxide and up to 20 wt. % of zinc oxide.

4 Claims, No Drawings

PROCESS FOR PREPARATION OF ALCOHOLS

FIELD OF THE INVENTION

The present invention relates to a process in which an organic carboxylic acid ester is reduced with hydrogen in the presence of a catalyst obtained by reducing a catalyst precursor comprising copper oxide or a composite metal oxide composed mainly of copper oxide and a carrier to obtain a corresponding alcohol.

BACKGROUND OF THE INVENTION

Many processes for preparing aliphatic alcohols, alicyclic alcohols or aromatic alcohols by hydrogenating carboxylic acids or carboxylic acid esters have been proposed since the 1930s.

Copper base catalysts have been mainly proposed as the catalyst for hydrogenation of carboxylic acid esters, especially fatty acid esters, and in general, a copper-chromium catalyst is preferably used on an industrial scale. However, the copper-chromium catalyst involves serious problems in connection with the disposal of waste water discharged from the catalyst-preparing process or the used catalyst, though the copper-chromium catalyst is excellent in catalyst performance. In the preparation of higher aliphatic alcohols where drastic reaction conditions are required for hydrogenation of carboxylic acid esters, and since high-temperature and high-pressure conditions such as a temperature of 250° to 300° C. and a pressure of 200 to 300 atmospheres are necessary for the preparation of higher aliphatic alcohols, there are various problems concerning equipment investment and maintenance. Moreover, since the reaction is carried out at a high temperature, formation of a side reaction product cannot be avoided, and use of this catalyst is not preferred from the energy-saving viewpoint.

Accordingly, development of a technique capable of hydrogenating a carboxylic acid ester at a low temperature or under a low pressure has been desired.

Attempts have been made to hydrogenate higher fatty acid esters at a low temperature or under a low pressure, but in most of these attempts, the intended object is attained by using a large quantity of a copper-chromium catalyst.

Adkins et al. report that in hydrogenating methyl laurate by the liquid-phase suspended bed reaction, lauryl alcohol is obtained at such a low temperature as 150° C. by using such a large amount of a copper-chromium catalyst such as 150 parts by weight per 100 parts by weight of the ester [J. Amer. Chem. Soc., 70, 3121 (1948)]. In this process, such a high hydrogen pressure as 340 atmospheres is adopted, and the reaction time is long though a large amount of the catalyst is used. Ueno et al. report that in hydrogenation of various fatty acid esters, aliphatic alcohols are obtained under low hydrogen pressure such as 10 to 25 atmospheres (initial charge pressure at room temperature) by using 10 parts by weight of a copper-chromium catalyst per 100 parts by weight of the ester [Kogyo Kagaku Zasshi, 38, 1105 (1935); ibid, 48,18 (1945)]. However, the reaction temperature is as high as 270° to 300° C., and the amount of unsaponified product formed by side reaction is large while the yield of the intended alcohol is very low and only 30 to 60%.

Japanese Patent Laid-Open No. 38333/1985 discloses an attempt to hydrogenate methyl laurate under reaction conditions of 218° C. and 60 bars by using copper-chromium as one component of the catalyst and adopting the fixed bed reaction method, but this process is defective in that the liquid hourly space velocity (LHSV) is 0.2 and productivity is very low.

Separately, catalysts not containing harmful chromium have been developed. For example, according to Japanese Patent Laid-Open No. 56139/1986, a higher fatty acid ester is hydrogenated under such a low pressure as 50 bars in the presence of a nickel catalyst by the fixed bed reaction. However, the reaction temperature is as high as 250° C. and the yield of the alcohol is very low and below 40%.

As is apparent from the foregoing description, according to any of the conventional techniques using a copper-chromium catalyst or a catalyst not containing harmful chromium, it is impossible to prepare a higher alcohol under low-temperature and low-pressure conditions by hydrogenation of a higher fatty acid ester while maintaining high productivity and high selectivity.

SUMMARY OF THE INVENTION

We made research with a view to developing a hydrogenation catalyst having a high activity at a low temperature and being suitable for hydrogenating a carboxylic acid ester under low-temperature and low-pressure reaction conditions to prepare a corresponding alcohol, and we have now completed the following catalyst not containing harmful chromium. Namely, to our great surprise, it was found that a copper-supported or copper/zinc-supported catalyst obtained by reducing a catalyst precursor comprising copper oxide or a composite metal oxide comprising copper oxide as the main component and a small amount of zinc oxide and a carrier has very high activity even under low-temperature and low-pressure reaction conditions, though attainment of such activity is very difficult according to conventional techniques.

Several attempts have been made to obtain higher alcohols by hydrogenating higher fatty acid esters in the presence of a copper-zinc composite oxide catalyst, which is one component of the catalyst developed by us. For example, there is known a process in which sperm oil is hydrogenated by the liquid-phase suspended bed reaction using a copper-zinc catalyst supported on diatomaceous earth [Kogyo Kagaku Zasshi, 53, 74 (1950)]. In this process, the reaction is carried out at 280° to 290° C. under a pressure of 110 atmospheres (the initial charge pressure at room temperature). According to German Patent No. 2,613,226, a methyl ester of a higher fatty acid is hydrogenated by the gas-phase fixed bed reaction using a copper-zinc solid catalyst. In this process, the reaction temperature is 230° to 240° C. and relatively low, but the pressure is as high as 250 atomospheres. Japanese Patent Laid-Open No. 32191/1979 discloses a process in which a methyl ester of a higher fatty acid is hydrogenated in the presence of a copper-molybdenum-zinc catalyst at 300° C. under a pressure of 95 atmospheres (the initial charge pressure at room temperature) by the liquid-phase suspended bed reaction, and in this process, the reaction conditions are very severe. According to the process disclosed in Japanese Patent Publication No. 45940/1985, a very large amount, 22 parts by weight, of a cobalt-zinc-copper catalyst is used per 100 wt. parts of the ester, and ethyl laurate is hydrogenated under conditions of 250° C. and 204 atmospheres. In this process, however, moderation of the reaction conditions is not sufficient. As is apparent from the foregoing illustration, according to the conventional technique, it is impossible to perform hydrogenation of higher fatty acid esters under low-temperature and low-pressure conditions even by using a copper-zinc type catalyst.

Japanese Patent Laid-Open No. 500993/1983 proposes a process for the hydrogenation of carboxylic acid esters in which relatively mild reaction conditions are adopted for the hydrogenation of a lower carboxylic acid ester. A typical instance of the weight composition of the copper-zinc catalyst used in this process is such that the amount of zinc oxide is 30 to 90%, and this composition is not substantially different from the composition in the already reported copper-zinc catalysts. It is taught that sodium, titanium, zirconium, manganese, silica, diatomaceous earth or aluminum oxide can be added as the third catalyst component in an amount of 0 to 20% by weight, but only the addition of aluminum oxide is disclosed in the examples and the effect attained by the addition is not mentioned at all.

In the catalyst proposed by us, it has been found that only in the case where in the catalyst precursor before activation by reduction, comprising copper oxide or a composite metal oxide comprising copper oxide as the main component and a small amount of zinc oxide, the amount of zinc oxide is 0 to 20% by weight and in the catalyst precursor comprising copper oxide or a composite oxide comprising copper oxide as the main component and a small amount of zinc oxide and a carrier, the amount of the carrier of titanium oxide and/or titanium hydroxide is 35 to 85% by weight, a high activity not expected from the heretofore proposed copper-zinc catalysts is manifested.

DETAILED DESCRIPTION OF THE PREFERRED EMBODIMENTS

The invention provides a process for producing an alcohol, which comprises the step of catalytically reducing an organic carboxylic acid ester with hydrogen in the presence of a catalyst obtained by reducing a catalyst precursor comprising (A) copper oxide and (B) titanium oxide and/or titanium hydroxide at a weight ratio of (A) to (B) in the range between 15/85 and 65/35. The component (A) may be alternatively a composite metal oxide comprising copper oxide and up to 20 wt. % of zinc oxide.

It is acceptable in the invention that component (A) is supported on component (B) or components (A) and (B) stand mixed with each other.

More specifically, in accordance with the present invention, there is provided a process for the preparation of alcohols, characterized by catalytically reducing an organic-carboxylic acid ester with hydrogen in the presence of a catalyst obtained by reducing a catalyst precursor comprising (A) copper oxide or a composite metal oxide comprising copper oxide and zinc oxide (copper oxide/zinc oxide weigh ratio=100/0 to 80/20), which is supported on (B) a carrier composed of titanium oxide and/or titanium hydroxide at an (A)/(B) weight ratio of from 15/85 to 65/35.

The process for the preparation of the catalyst precursor composition of the present invention is not particularly critical, but known processes can be adopted. For example, the catalyst precursor composition is prepared according to a process in which a precipitate obtained by the co-precipitation method of adding a precipitating agent to a mixed aqueous solution containing metal salts or adding a precipitating agent to an aqueous solution of metal salts other than the carrier component in the presence of a fine powder of the carrier is water-washed, dried and calcined or a process in which a fine powder of the carrier is impregnated with an aqueous solution of metal salts of catalyst components other than the carrier component and the impregnated carrier is dried and calcined.

In the case where the catalyst precursor composition is prepared according to the precipitation process or impregnation process, all of water-soluble metal salts can be used. For example, as the copper and zinc salts, there can generally be used sulfates, nitrates, ammonium complex salts, acetates, oxalates and chlorides, and sulfates are used as the titanium salt.

As the titanium oxide and/or titanium hydroxide, there can be used titanium oxides such as $TiO_2$ (titania), $TiO$ and $Ti_2O_3$, metatitanic acid $[TiO(OH)_2]$, titanic acid $[Ti(OH)_4]$ and mixtures thereof, and a compound having a large surface area is preferred. The carrier can be prepared by hydrolysis of a sulfate, chloride or alkoxide or by precipitation from an aqueous solution of a sulfate.

As the precipitating agent used in the precipitation process, there can be mentioned an aqueous solution of an alkaline substance such as ammonia, urea, ammonium carbonate, sodium carbonate, sodium hydrogencarbonate, sodium hydroxide or potassium hydroxide.

In the case where the composite metal oxide is prepared according to the co-precipitation process, adjustment of the pH value and selection of the calcination temperature are important. For example, the pH value is preferably adjusted to 2 to 11, and it is preferred that the calcination be carried out at 300° to 600° C.

In order to improve the catalyst strength or the like, a minute amount of a third component such as graphite, a fatty acid salt, starch, mineral oil, talc, bentonite, an alkali metal salt or an alkaline earth metal salt can be added to the obtained catalyst precursor, so far as attainment of the effect of the present invention is not hindered.

In the present invention, the composition of the catalyst is important.

More specifically, it is important that in the catalyst precursor before activation by reduction, the amount of zinc oxide should be 0 to 20% by weight, preferably 1 to 15% by weight, in copper oxide or the composite metal oxide comprising copper oxide as the main component and a small amount of zinc oxide, and that in the catalyst precursor comprising copper oxide or the composite metal oxide comprising copper oxide as the main component and a small amount of zinc oxide and the carrier, the amount of the carrier of titanium oxide and/or titanium hydroxide should be 35 to 85% by weight. If any one of these conditions is not satisfied, the catalyst performance is drastically degraded.

In the present invention, if the abovementioned composition requirements are satisfied, even a simple mixture of the components (A) and (B) is effective as the catalyst (catalyst precursor), but it is preferred that component (A) be supported on component (B).

In the case where zinc oxide is added as the catalyst component, there can be adopted a process in which the zinc component is incorporated together with the copper component by the co-precipitation, or a process in which copper oxide is supported on titanium oxide in advance and a predetermined amount of the zinc oxide component is incorporated by the precipitation or impregnation method.

The activation of the catalyst precursor by the reduction is necessary for the hydrogenation of a carboxylic acid ester. In the case where the catalyst precursor is activated by the reduction, there can be adopted a gas-phase reduction process or a liquid-phase reduction process in which the reduction is carried out in a solvent, for example, a hydrocarbon such as liquid paraffin, dioxane, an aliphatic alcohol or a fatty acid ester. For example, in the case where the reduction is carried out by using hydrogen gas, it is preferred that the reduction be conducted at 100° to 800° C., especially 150° to 500° C., until formation of water ceases or absorption of hydrogen is not observed. In the case where the reduction is carried out in a solvent, it is preferred that the reduction be conducted at a temperature of 150° to 350° C. until absorption of hydrogen is not observed. Moreover, an ordinary activation process in which the temperature of the catalyst precursor is elevated in the ester to be hydrogenated in an atmosphere of hydrogen to effect the reduction and the system is directly subjected to the reaction can be adopted without any trouble.

As the reducing agent for reducing the catalyst precursor, there can be used not only the above-mentioned hydrogen, but also carbon monoxide, ammonia, hydrazine, formaldehyde and a lower alcohol such as methanol. These reducing agents can be used singly or in the form of a mixture of two or more of them. The reducing agent can be used in the state diluted with an inert gas such as nitrogen, helium or argon or in the presence of a small amount of steam.

As the organic carboxylic acid ester to be hydrogenated in the present invention, there can be mentioned esters of linear, branched and unsaturated fatty acids having at least one carbon atom and at least one ester group, esters of alicylic carboxylic acid and esters of aromatic carboxylic acids. The alcohol portion constituting the carboxylic acid ester is not particularly critical. As examples of the carboxylic acid ester, there can be mentioned formic acid esters, acetic acid esters, caproic acid esters, caprylic acid, undecenoic acid esters, lauric acid esters, myristic acid esters, palmitic acid esters, stearic acid esters, isostearic acid esters, oleic acid esters, oxalic acid esters, maleic acid esters, adipic acid esters, sebacic acid esters, cyclohexane-carboxylic acid esters, benzoic acid esters and phthalic acid esters.

For the hydrogenation of the carboxylic acid ester, the suspended bed reaction, the fixed bed reaction or the fluidized bed reaction can be adopted according to the shape of the catalyst.

For example, a powdery catalyst is used when the suspended bed reaction is adopted. A solvent can be used for the reaction, but in view of productivity, it is preferred that the reaciton be carried out in the absence of a solvent. Solvents having no bad influences on the reaction, such as an alcohol, dioxane and a hydrocarbon, are selected and used. In this case, it is preferred that the amount of the catalyst be 0.1 to 20% by weight based on the carboxylic acid ester, but according to the reaction temperature and reaction pressure, the amount of the catalyst is selected so that a practical reaction speed is obtained. The reaction temperature is 160° to 350° C., preferably 200° to 280° C., and the reaction pressure is 1 to 350 kg/cm$^2$, preferably 30 to 300 kg/cm$^2$.

In the case where the fixed bed reaction is adopted, the catalyst molded in the shape of a column, a pellet or a sphere is used. The reaction temperature is 130° to 300° C., preferably 160° to 270° C., and the reaction pressure is 0.1 to 300 kg/cm$^2$. The liquid hourly space velocity (LHSV) is optionally determined according to the reaction conditions, but in view of productivity and reactivity, it is preferred that the liquid hourly space velocity (LHSV) be 0.5 to 5.

(EXAMPLES)

The present invention will now be described in detail with reference to the following Examples that by no means limit the scope of the invention.

EXAMPLE 1

Preparation of Catalyst

A hydrolysis product of tetraisopropyl titanate $\{[(CH_3)_2CHO]_4Ti\}$ as the starting material of the carrier, a mixed aqueous solution of copper nitrate and zinc nitrate and an aqueous solution containing 10% by weight of sodium carbonate were mixed and stirred at 98° C. to obtain a slurry having a pH value of 9. The precipitate was recovered from the slurry by filtration, washed with water, dried and calcined at 450° C. for 2 hours to obtain a copper oxide/zinc oxide composite oxide supported on titanium oxide. The obtained composite oxide was expressed by the following weight composition:

$CuO:ZnO:TiO_2 = 47.5\%:2.5\%:50.0\%(95.0\%:5.0\%)$

The parenthesized value indicates the weight ratio of copper oxide to zinc oxide.

Evaluation of Catalyst Activity

A 0.5-liter autoclave equipped with a rotary stirrer was charged with 150 g of a methyl ester of a fatty acid having an alkyl composition of 8 to 18 carbon atoms (saponification value SV=258, acid value AV=0.06) and 3.75 g of the so-prepared catalyst precursor (2.5% by weight based on the ester), and the reduction activation of the catalyst precursor was carried out under a hydrogen pressure of 10 kg/cm$^2$ (gauge pressure) at a temperature of 200° C. for 2 hours in circulation of hydrogen. Then, the temperature was elevated to 230° C. and the hydrogen pressure was elevated to 120 kg/cm$^2$, and the reaction was started at a stirring speed of 800 rpm and a hydrogen flow rate of 5 l/min.

The catalyst activity was evaluated based on the primary reaction rate constant per gram of the catalyst precursor or the time (Tsv=6) required for arrival at SV=6* (*: equilibrium SV=5 under conditions of 230° C. and 120 kg/cm$^2$).

The obtained results are shown in Table 1.

EXAMPLES 2 THROUGH 4 AND COMPARATIVE EXAMPLES 1 AND 2

A catalyst precursor comprising copper oxide or copper oxide-zinc oxide supported on titanium oxide was prepared in the same manner as described in Example 1 except that the amount of zinc oxide was changed. By using the obtained catalyst, the methyl ester of the fatty acid was hydrogenated according to the catalyst activity-evaluating method described in Example 1.

The obtained results are shown in Table 1.

TABLE 1

| | CuO:ZnO:TiO$_2$ (CuO:ZnO) | Catalyst concentration [% by weight] | k [Hr$^{-1}$·gr$^{-1}$] | Tsv = 6 [Hr] |
|---|---|---|---|---|
| Example 2 | 50:0:50 (100:0) | 5.0 | 0.44 | 2.63 |
| Example 3 | 49:1:50 (98:2) | 2.5 | 0.88 | 2.40 |
| Example 1 | 47.5:2.5:50 (95:5) | 2.5 | 1.11 | 1.70 |
| Example 4 | 45:5:50 (90:10) | 2.5 | 0.67 | 2.37 |
| Comparative Example 1 | 37.5:12.5:50 (75:25) | 5.0 | 0.067 | SV = 15 at 3 Hr |
| Comparative Example 2 | 30:20:50 (60:40) | 5.0 | 0.043 | SV = 30 at 3 Hr |

COMPARATIVE EXAMPLES 3 and 4

Two catalyst precursors differing in the composition of copper oxide and zinc oxide were prepared in the same manner as described in Example 1 except that the carrier was not used. By using these catalyst precursors, the methyl ester of the fatty acid was hydrogenated according to the catalyst activity-evaluating method described in Example 1.

The obtained results are shown in Table 2.

TABLE 2

| | CuO:ZnO | Catalyst concentration (% by weight) | k [Hr$^{-1}$·gr$^{-1}$] | Tsv = 6 [Hr] |
|---|---|---|---|---|
| Comparative Example 3 | 90:10 | 5.0 | 0.20 | SV = 9 at 3 Hr |
| Comparative Example 4 | 60:40 | 5.0 | 0.23 | 2.20 |

As is apparent from the results shown in Tables 1 and 2, the effect of the titanium oxide carrier is specifically attained only when the catalyst composition requirements of the present invention are satisfied. On the other hand, in copper-zinc catalysts having heretofore proposed compositions, an inhibitory effect is observed.

EXAMPLES 5 AND 6 AND COMPARATIVE EXAMPLES 5 AND 6

Catalyst precursors comprising copper oxide and zinc oxide at a weight ratio of 90/10 were prepared in the same manner as described in Example 1 except that the amount of the titanium oxide carrier was changed. By using these catalyst precursors, the methyl ester of the fatty acid was hydrogenated according to the catalyst activity-evaluating method described in Example 1. The catalyst concentration was adjusted to 5.0% by weight.

The obtained results are shown in Table 3.

TABLE 3

| | CuO:ZnO:TiO$_2$ (CuO:ZnO) | Catalyst concentration [% by weight] | k [Hr$^{-1}$·gr$^{-1}$] | Tsv = 6 [Hr] |
|---|---|---|---|---|
| Comparative Example 5 | 67.5:7.5:25 (90:10) | 5.0 | 0.21 | 2.53 |
| Example 5 | 45:5:50 (90:10) | 5.0 | 0.61 | 1.37 |
| Example 6 | 22.5:2.5:75 (90:10) | 5.0 | 0.45 | 2.70 |
| Comparative Example 6 | 9:1:90 (90:10) | 5.0 | 0.061 | SV = 80 at 3 Hr |

EXAMPLE 7

By using the catalyst precursor described in Example 1, the methyl ester of the fatty acid was hydrogenated according to the same catalyst activity-evaluating method as described in Example 1 except that the reaction temperature was changed to 220° C.

The obtained results are shown below.

k=0.79[Hr$^{-1}$·gr$^{-1}$]

Tsv=6=2.83Hr

COMPARATIVE EXAMPLE 7

By using 5.0% by weight of a commercially available copper-chromium catalyst, the methyl ester of the fatty acid was hydrogenated according to the catalyst activity-evaluating method described in Example 1. The obtained results are shown below.

k=0.34[Hr$^{-1}$·gr$^{-1}$]

Tsv=6=3.00Hr

We claim:

1. A process for producing an alcohol, which comprises the step of catalytically reducing an organic carboxylic acid ester with hydrogen in the presence of a catalyst obtained by reducing a catalyst precursor comprising (A) copper oxide and (B) titanium oxide and/or titanium hydroxide at a weight ratio of (A) to (B) in the range between 15/85 and 65/35.

2. The process as claimed in claim 1, wherein said component (A) is a composite metal oxide comprising copper oxide and up to 20 wt. % of zinc oxide.

3. The process as claimed in claim 1 or 2, wherein said the component (A) is supported on the component (B).

4. The process as claimed in claim 1 or 2, wherein said components (A) and (B) stand mixed with each other.

* * * * *